United States Patent [19]

Naef et al.

[11] Patent Number: 5,086,038
[45] Date of Patent: Feb. 4, 1992

[54] AROMATIC ALDEHYDES, THEIR DERIVATIVES AND THEIR UTILIZATION AS PERFUMING INGREDIENTS

[75] Inventors: Ferdinand Naef; François Delay, both of Carouge, Switzerland; Arnoldus Uijttewaal, St-Genis/Pouilly, France

[73] Assignee: Firmenich SA, Geneva, Switzerland

[21] Appl. No.: 670,653

[22] Filed: Mar. 18, 1991

Related U.S. Application Data

[62] Division of Ser. No. 503,339, Apr. 2, 1990.

[30] Foreign Application Priority Data

Apr. 12, 1989 [CH] Switzerland ............... 1379/89

[51] Int. Cl.⁵ .................................................. A61K 7/46
[52] U.S. Cl. ........................................ 512/21; 512/20; 252/8.6; 252/174.11; 424/76.4
[58] Field of Search ............... 512/20, 21; 252/174.11, 252/8.6; 424/76.4

[56] References Cited

U.S. PATENT DOCUMENTS

| | | | |
|---|---|---|---|
| 2,976,327 | 3/1961 | Dorsky et al. | 512/20 |
| 3,922,237 | 11/1975 | Schreiber et al. | 512/20 |
| 4,113,781 | 9/1978 | Aquila et al. | 512/21 |
| 4,910,346 | 3/1990 | Chalk | 512/21 |

*Primary Examiner*—James H. Reamer
*Attorney, Agent, or Firm*—Pennie & Edmonds

[57] ABSTRACT

Aromatic aldehydes of formula

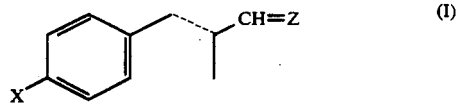

possessing a single or a double bond in the position indicated by the dotted line and wherein symbol X represents a monovalent radical or formula

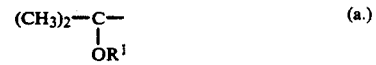

or, when the dotted line represents a single bond, of formula

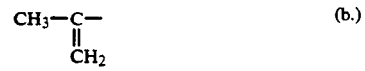

and wherein symbol Z stands for an oxygen atom or for two $R^2O$ radicals, each of $R^1$ and $R^2$ representing an alkyl radical having from 1 to 3 carbon atoms.

Aromatic aldehydes (I) possess useful odorous properties and can be used as perfuming ingredients for the preparation of perfume bases and perfumed articles. They can also be used as starting materials for the preparation of useful end-products having herbicide and fungicide properties.

Process for the preparation of aromatic aldehydes (I) starting from 8-methoxycuminic aldehyde.

13 Claims, No Drawings

AROMATIC ALDEHYDES, THEIR DERIVATIVES AND THEIR UTILIZATION AS PERFUMING INGREDIENTS

This is a division of application Ser. No. 07/503,339 filed Apr. 2, 1990.

BRIEF SUMMARY OF THE INVENTION

The present invention relates to the field of perfumery, in particular to novel aromatic aldehydes and to their derivatives, which compounds are defined by the following general formula

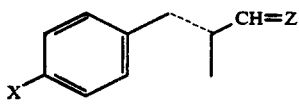 (I)

possessing a single or a double bond in the position indicated by the dotted line and wherein symbol X represents a monovalent radical or formula

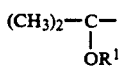 (a.)

or, when the dotted line represents a single bond, of formula

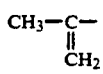 (b.)

and wherein symbol Z stands for an oxygen atom or for two $R^2O$ radicals, $R^1$ and $R^2$ representing an alkyl radical having from 1 to 3 carbon atoms.

This invention relates also to the utilization of the said aromatic aldehydes and derivatives thereof as perfume ingredients for the preparation of perfume bases and perfumed articles.

Further, the invention relates to a process for the preparation of the said compounds which process is characterized by the following reaction steps:
a. addition of propanal to 8-methoxycuminic aldehyde to give 3-[4-(1-methoxyl-1-methylethyl)-1-phenyl]-2-methyl-2-propenal;
b. reduction of the thus formed compound by catalytic hydrogenation in the presence of a metal catalyst to give 3-[4-(1-methoxy-1-methylethyl)-1-phenyl]-2-methylpropanal;
c. treatment of the resulting compound with a strong acidic agent to give 3-(4-isopropenyl-1-phenyl)-2-methylpropanal, and, if desired,
d. conversion of the two aldehydes obtained according to letter b. or c. above to their corresponding acetal derivatives according to the current methods.

Further, the present invention relates to novel fungicides and herbicides of formula

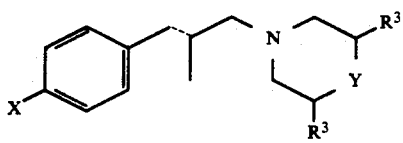 (II)

processing a single or a double bond in the position indicated by the dotted line and wherein symbol X represents a monovalent radical or formula

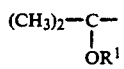 (a.)

$R^1$ representing an alkyl radical having from 1 to 3 carbon atoms, or, when the dotted line represents a single bond, of formula

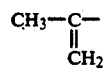 (b.)

symbol Y represents a methylene radical or an oxygen atom and $R^3$ designates a hydrogen atom or a methyl radical.

BACKGROUND OF THE INVENTION p-tert-Butyl-α-methyl-hydrocinnamic aldehyde, and its lower homolog alike, cyclamen aldehyde, has known an ever growing success in perfumery since its discovery (see U.S. Pat. No. 2,875,131). Commercialized under different brand names, this aldehyde has found a particular utilization in the creation of flowery compositions where it matches harmoniously with woody and musky components. In view of its interest, several research groups have investigated over the years various synthetic methods and have proposed a variety of structural analogs for its replacement; sofar, however, without tangible success. Surprisingly, we have discovered that the compounds of formula (I) possessed exceptional odorous properties and that consequently they could find an advantageous utilization in perfumery.

THE INVENTION

The main object of the present invention relates to novel aromatic aldehydes and derivatives thereof of formula (I). The odor character of the said compounds, while belonging to that of the odor family of the known p-tert-butyl-α-methyl-hydrocinnamic aldehyde for its floral connotation, differs from that of the known compound for the presence of a distinct white flower fragrance of lily-of-the-valley type. Compounds (I), moreover, possess a sweet note more flowery and less green-aqueous than the said known aldehyde as well as an elegant velvety nuance. The floral note is fresher and the white flower character is less aggressive than that of known compounds; their use therefore is broader.

The more pronounced characters are shown by 3-[4-(1-methoxy-1-methylethyl)-1-phenyl]-2-methylpropanal.

3-(4-Isopropenyl-1-phenyl)-2-methylpropanal, on the contrary, is characterized by a greener note of green melon type. It is reminiscent of cyclamen aldehyde; however, it is less acidic and less aldehydic than the odor developed by the said known compound and shows a citrus fruit character of which cyclamen aldehyde is deprived. Besides this compound of the invention possesses a slightly flour character which, in some way, is reminiscent of neroli oil.

Nothing in the state of the art indicated or suggested that the compounds of the invention could present such useful properties nor was there any hint on the possibility to synthesize them.

Owing to their useful odorous properties, compounds (I) can be used to perfume a variety of articles and can be used for the creation of perfumes and perfumed bases. Their utility is very broad. Among the articles which can be perfumed by compounds (I), one can cite for example soaps, solid and liquid detergents of ionic, anionic, zwitterionic or non-ionic type, fabric softeners, household materials as well as cosmetics, shampoos, body deodorizers. When used in conjunction with polymeric bases or resin supports, the aromatic aldehydes of the invention can be used as active principles for the manufacture of air-fresheners or closed room deodorizers. The proportions in which aromatic aldehydes (I) can develop the desired odorous characters can of course vary within a wide range. The man of the art knows by experience that these values depend on the specific effect it is desired to achieve and on the nature of the material it is desired to perfume. These values depend also on the nature of the other constituents in a given composition whenever aldehydes (I) are used in the preparation of perfumes or perfumed bases, usually in a concentrated form in admixture with other perfume coingredients, solvents or current adjuvants.

Suitable coingredients belong to various chemical families; they are for example aldehydes, esters, ethers or alcohols. They can be of natural or synthetic origin. The specific comprehensive mention of these coingredients is here superfluous. The state of the art is in effect rich of examples and the expert can choose among the known ingredients those which at best might satisfy his objective of creation. A particular reference is here made to S. Arctander, Perfume and Flavor Chemicals, Montclair, N.J., U.S.A. (1969).

Due to their odor strength, aldehydes (I) can be used at concentrations varying from about 1 to about 20 or 25% by weight based on the total weight of the composition into which they are incorporated. Of course, when compounds (I) are used to perfume consumer products such as those mentioned above, the concentrations values are lower and can be of the order of 0.5–1.0% by weight.

The values of concentrations indicated above must be interpreted in a non restrictive manner and values other than those indicated can be used whenever special effects are desired.

As said above, the compounds of the invention are new chemical entities. They can be synthesized according to a multistep process consisting in carrying out subsequent distinct steps, each of them being analogous to prior known processes starting from 4-(1-methoxy-1-methylethyl)-benzaldehyde, a product commercially available [origin: BAS AG, Ludwigshafen/Rh. (FRG); see European patent application published under n° 275489].

The process consists in
a. the addition of propanal to 8-methoxycuminic aldehyde to give 3-[4-1-methoxy-1-methylethyl)-1-phenyl]-2-methyl-2-propenal;
b. the reduction of the thus formed compound by catalytic hydrogenation in the presence of a metal catalyst to give 3-[4-(1-methoxy-1-methylethyl)-1-phenyl]-2-methylpropanal;
c. the treatment of the resulting compound with a strong acid agent to give 3-(4-isopropenyl-1-phenyl)-2-methylpropanal, and, if desired,
d. the conversion of the two aldehydes obtained according to letter b. or c. above to their corresponding acetal derivatives according to the current methods.

The first step of this process is carried out in a basic medium, preferably in the presence of a strong base such as an alkali metal hydroxide, for instance potassium hydroxide in an alcoholic solution, preferably methanol.

Concerning the reduction step, this is carried out by a catalytic hydrogenation in the presence of a metal catalyst such as those currently used to promote the reduction of an ethylene double bond. Preferably, palladium is used, e.g. palladium on a solid support, for instance alumina. 3-[4-(1-Methoxy-1-methylethyl)-1-phenyl]-2-methylpropanal is thus obtained. By acidification of this product, there is obtained the corresponding demethoxylated compound, or 3-(4-isopropenyl-1-phenyl)-2-methylpropanal.

The conversion of this latter compound into its corresponding acetal, as well as the formation of acetal derivatives of 3-[4-(1-methoxy-1-methylethyl)-1-phenyl]-1-phenyl]-2-methylpropanel, are carried out according to current method known in the art. For instance, treatment of the said aldehydes with trialkyl orthoformate in a medium constituted by lower aliphatic alcohols gives the desired acetals with quantitative yields. Specific examples of preparation will be given further on.

The compounds of the invention find a utility not only as perfume ingredients as specified above but also as starting materials for the preparation of useful end-products having fungicide or herbicide properties.

This invention relates also to this specific utilization and provides further new active compounds. These belong to the class of nitrogen heterocyclic derivatives of general formula

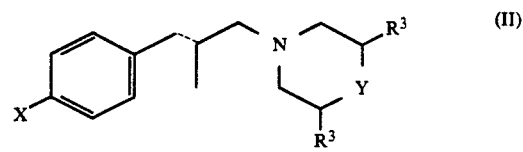

wherein X and the dotted line are defined as indicated for formula (I), symbol Y designates an oxygen atom or a methylene radical and $R^3$ represents a hydrogen atom or a methyl radical. Specific examples of the compounds defined by formula (II) include the following:

N-{3-[4-(1-methoxy-1-methylethyl)-1-phenyl]-2-methylpropyl}-morpholine,

N-{3-[4-(1-methoxy-1-methylethyl)-1-phenyl]-2-methylpropyl}-piperidine,

N-{3-[4-(1-methoxy-1-methylethyl)-1-phenyl]-2-methylpropyl}-2,6-dimethylmorpholine, N-[-3-(4-isopropenyl-1-phenyl)-2-methylpropyl]-piperidine, and N-[-3-(4-isopropenyl-1-phenyl)-2-methylpropyl]-morpholine.

Compounds (II) showed good preventive fungicidal activity against rust on bean and wheat as well as powdery mildew on grape and wheat. These compounds were also active against powdery mildew on barley. No plant damage was observed within the experimental dosage applied (lower than or equal to 125 mg ai/lt).

Compounds (II) could be utilized at concentrations varying from 5 to 500 mg per liter of active broth. Their active concentrations when applied in the field is of the order of 100 g to 2500 g of active substance (II) per hectar (=2.5 acres).

As indicated above, compounds of formula (II) are new chemical entities. Their preparation is carried out in accordance with synthetic methods analogous to prior known processes starting from aldehydes of formula (I) by treatment with a nitrogen heterocyclic derivative of formula

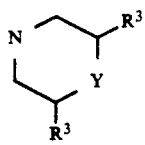

wherein symbol Y and substituent R³ are defined as indicated above. The preparation is usually carried out at room temperature, preferably in an inert organic medium constituted by an aromatic hydrocarbon, for instance toluene. Specific details of their preparation will be given in the examples which follow.

The invention is illustrated by but not limited to the following examples wherein the temperatures are indicated in degrees centigrade and the abbreviations have the meaning common in the art.

EXAMPLE 1

Preparation of
3-[4-(1-methoxy-1-methylethyl)-1-phenyl]-2-methylpropanal a. (E)-3-[4-(1-methoxy-1-methylethyl)-1-phenyl]-2-methyl-2-propenal 552 g (9.5 mole) of propanal were slowly added to a stirred mixture of 1000 g (5.6 mole) of 8-methoxycuminic aldehyde [origine: BASF AG, Ludwigshafen/Rh, (FRG)], 172 g of aqueous KOH at 45% and 3360 g of methanol. The reaction is slightly exothermic and at the end of the addition the temperature of the mixture raised to 35°. The mixture is kept under stirring for one further hour than its pH was adjusted to 7.5 by the addition of acetic acid and methanol was stripped off at ordinary pressure. After cooling at 60°, 810 g of water were added while the salts which have precipitated dissolved under stirring during 30 min. The separated organic phase was distilled on a Vigreux column of 15 cm length at a pressure of 0.1 mbar. 906 g (4.15 mole) of the desired aldehyde were obtained under the form of a yellow liquid having b.p. 110°-114° (yield 74%).

MS: M+=218(3); m/z: 203(65), 186(34), 171(11), 145(100), 128(37), 115(72), 103(9), 91(26), 77(13), 63(9), 51(8), 43(16),

¹HNMR(360 MHz): 1.56(6H,s); 2.11(3H,s); 3.11(3H,s); 7.27(1H, broad s); 7.50 and 7.54(4H,2d); 9.59(1H,s) δ ppm;

¹³CNMR:10.9(q); 27.8(2q); 76.8(s); 126.2(2d); 130.1(2d); 133.8(s); 138.2(s); 148.0(s); 149.5(d); 195.6(d) δ ppm;

IR: 1660, 1620 and 1600 cm⁻¹.

b. 3-[4-(1-methoxy-1-methylethyl)-1-phenyl]-2-methylpropanal 160 g (0.733 mole) of the aldehyde prepared according to the method described under letter a. above in admixture with 1 g of palladium on alumina (5%), 0.1 g of potassium acetate and 2 g of water were introduced into a 500 bar for 3 h. After cooling and filtration, the raw material (155 g) was distilled on a column filled with glass helixes (length: 10 cm). 145 g (0.66 mole) of the desired aldehyde were obtained in the form of a colorless liquid having b.p. 82°-85° mbar (yield 90%).

MS: M+=200(1); m/z: 205(100), 189(16), 161(4), 148(47), 131(98), 115(38),

¹H NMR(360 MHz): 0.92(3H,d,³J=7.2); 1.32(6H,s); 1.74(1H,broad s); 2.41(1H,dd,²J=7.6); 2.75(dd,²J=11.9,³J=6.9); 3.06(3H,s); 3.49(2H,broad m); 7.14 and 7.32(4H,2d) δ ppm;

¹³CNMR:16.6(q); 27.9(2q); 39.3(t); 50.6(q);67.5(t); 76.7(s); 125(2d); 129.0(2d); 139.3(s); 143.4(s) δ ppm;

IR: 3400 cm⁻¹.

EXAMPLE 2

Preparation of
3-(4-isopropenyl-1-phenyl)-2-methylpropanal 55 g (0.25 mole) of 3-[4-(1-methoxy-1-methylethyl-1-phenyl]-2-methylpropanal were slowly added to 660 ml of a 10% solution of sulphuric acid preheated at 95° and while a flow of vapor of 3 kg/h was bubbled through. Once the addition was over and the vapor phase distillation ceased, the liquors were extracted with diethyl ether and the organic phase was dried and evaporated. 45 g of raw material was thus obtained and distilled on an helixes filled column of 10 cm length. 40 g of a colorless liquid were obtained with a purity of 98% (yield 85%). B.p. 127°-130°/0.1 mbar.

MS: M+=188(22); m/z: 173(3), 155(2), 145(7), 131(100), 115(26), 104(4), 91(33), 77(8), 65(5), 51(4), 51(5);

¹H NMR(360 MHz): 1.10(3H,d,³J=7.2); 2.14(3H,s); 2.61(1H,dd,²J=11.8,³J=7.8); 2.66(1H,m); 3.08(1H,dd,²J=7.0); 5.06(1H,s); 5.35(1H,s); 7.13 and 7.40(4H,2d)δppm;

¹³C NMR: 13.3(q); 36.4(t); 48.0(d); 112.1(t); 125.7(2d); 128.9(2d); 138.1(s); 139.7(s); 204.1(d) δ ppm;

IR: 1715 and 1620 cm⁻¹.

EXAMPLE 3

3-[4-(1-Methoxy-1-methylethyl)-1-phenyl]-2-methylpropionaldehyde dimethylacetal

A mixture of 2.03 g (9.23 mM) of 3-[4-(1-methoxy-1-methylethyl)-1-phenyl]-2-methylpropanal, 1.09 g (10.3 mM) of trimethylorthoformate, 20 ml of dry methanol and 20 mg of ammonium chloride was stirred in a round-bottomed flask and kept 18 h at room temperature. The reaction mixture was poured into a 5% aqueous solution of sodium bicarbonate and extracted twice with ether. The combined organic extracts were washed twice with brine, concentrated on a rotary evaporator and distilled on residue to give a fraction of 2.33 g (yield 95%) of the desired acetal having b.p. 130° (bath temp.)/0.1 mbar.

MS: M+=266(1); m/z: 251(6), 234(16), 219(46), 202(45), 187(39), 155(25), 131(32), 75(100), 43(18);

¹HNMR(360 MHz): 0.85(3H,d,J=6.5); 1.52(6H,s); 3.06(3H,s); 3.8 and 4.0(6H,s); 4.08(1H,d,J=6.5); 7.14 and 7.32(4H,2d,J=8) δ ppm.

By following the same procedure as that indicated above, the following acetal derivatives were prepared:

| end-product | starting material | reactant |
|---|---|---|
| (a) | (b) | triethylformate |
| (c) | (d) | trimethylformate |
| (e) | (d) | triethylformate |

(a) = 3-[4-(1-methoxy-1-methylethyl)-1-phenyl]-2-methylpropionaldehyde diethylacetal
(b) = 3-[4-(1-methoxy-1-methylethyl)-1-phenyl]-2-methylpropanal
(c) = 3-(4-isopropenyl-1-phenyl)-2-methylpropionaldehyde dimethylacetal -continued (d) = 3-(4-isopropenyl-1-phenyl)-2-methylpropanal
(e) = 3-(4-isopropenyl-1-phenyl)-2-methylpropionaldehyde diethylacetal (a):
MS: M+ = 294(0); m/z: 279(1),248(12),233(25),216(34),131(46), 103(100),75(41),43(39);
¹HNMR(360MHz): 0.86(3H, d , J=6.5); 1.22(6H, t, J=7); 1.52(6H, s); 3.06(3H, s); 3.54 and 3.7(4H, 2m); 4.22(1H, d, J=6.5); 7.13 and 7.32(4H, 2d, J=8) δ ppm.

(c):
MS: M+ = 234(2); m/z: 202(38),187(37),155(21),131(45), 115(22),91(21),75(100);
¹HNMR(360MHz): 0.85(3H, d, J=6.5); 2.14(3H, s); 3.38 and 3.39(6H, 2s); 4.06(1H, d, J=6.5); 5.04 and 5.36(2H, 2s); 7.12 and 7.38(4H, 2d, J=8) δ ppm.

(e):
MS: M+ = 262(1); m/z: 216(63),131(98),103(100), 75(75),43(95);
¹HNMR(360MHz): 0.86(3H, d, J=6.5); 1.23(6H, t, J=7); 2.14(3H, s); 3.52 and 3.68(4H, m); 4.21(1H, d, J=6.5); 5.04 and 5.35(2H, 2s); 7.12 and 7.38(4H, 2d, J=8) δ ppm.

(a)=3-[4-(1-methoxy-1-methylethyl)-1-phenyl]-2-methylpropionaldehyde diethylacetal
(b) 3-[4-(1-methoxy-1-methylethyl)-1-phenyl]-2-methylpropanal
(c)=3-[(4-isopropenyl-1-phenyl)-2-methylpropionaldehyde dimethylacetal
(d)=3-(4-isopropenyl-1-phenyl)-2-methylpropanal
(e)=3-(4-isopropenyl-1-phenyl)-2-methylpropionaldehyde diethylacetal (a): MS: M+=194(0); m/z: 179(1), 248(12), 233(25), 216(34), 103(100), 75(41), 43(39);
¹H NMR(360 MHz): 0.86(3H,d,J=6.5); 1.22(6H,t,J=7), 1.52(6H,s); 3.06(3H,s); 3.54 and 3.7(4H,2m); 4.22(1H,d,J=6.5); 7.13 and 7.32(4H,2d,J=8) δ ppm.

(c): MS: M+=234(2); m/z: 202(38), 187(37), 155(21), 131(45), 115(22), 91(21), 75(100);
¹H NMR(360 MHz): 0.85(3H,d,J=6.5); 2.14(3H,s); 3.38 and 3.39(6H,2s); 4.06(1H, d,J=6.5); 5.04 and 5.36(2H,2s); 7.12 and 7.38(4H,2d,J=8) δ ppm.

(e): MS:M+=262(1); m/z: 216(63), 131(98), 103(100), 75(75), 43(95);
¹H NMR(360 MHz): 0.86(3H,d,J=6.5); 1.23(6H,t,J=7); 2.14(3H,s); 3.52 and 3.68(4H,m); 4.21(1H,d,J=6.5); 5.04 and 5.35(2H,2s); 7.12 and 7.38(4H,2d,J=8) δ ppm.

EXAMPLE 4

N-{3-[4-(1-Methoxy-1-methylethyl)-1)]-2-methylpropyl}-2,6-dimethylmorpholine 0.63M of dimethylmorpholine were added at room temperature to a solution of 0.48M of 3-(-4-(1-methoxy-1-methoxy-1-methylethyl)-1)-1-phenyl]-2-methylpropanal in 100 ml of toluene in a reaction vessel equipped with a Dean-Stark separator. The reaction is slightly exothermic. The mixture was then heated at reflux for about 4 h then cooled to room temperature.

The solution was directly transferred in a hydrogenation flask where it was subjected to hydrogenation at atmospheric pressure in the presence of 15 g of 5% palladium on charcoal. After the adsorption of 1 equivalent of hydrogen, the catalyst is recovered by filtration, toluene was stripped off and the residue was distilled at reduced pressure. The desired product was obtained with a yield of 75%.

B.p. 112°/0.1 mbar.
IR: 3000–2600, 1900–1590 cm⁻¹;
MS: m/z: 128(100), 43(8), 70(8), 129(8), 159(2), 84(2), 55(1), 145(1), 319(1);
¹HNMR(360 MHz): 0.85(3H,d,J=7); 1.15[1]) and 1.23/1.26[2]) (6H,d,J=6.8); 1.52(6H,s); 1.68(2H,q,J=10); 1.9–2.45(5H,m); 2.63–2.82(2H,m); 3.06(3H,s); 3.68 [1])and 4.22[2]) (2H,m); 7.12 and 7.31(4H,AB,J=7.2) δ ppm.

[1]) cis-isomer
[2]) trans-isomer

By following the same procedure as that described above, the following compounds were obtained:

N-{3-[4-(1-methoxy-1-methylethyl)-1-phenyl]-2-methylpropyl}-morpholine:
B.p. 115°/0.1 mbar.
IR: 3100–2700, 1900–1590 cm⁻¹;
MS: M+=291(0.5); m/z: 100(100), 56(5), 91(2), 70(2), 43(2), 115(1), 161(1), 173(1);
¹HNMR(360 MHz): 0.85(3H,d,J=7); 1.52(6H,s); 1.97(1H,m); 2.16(2H,m); 2.26–2.45(5H,m); 2.80(1H,dd,¹J=12.5,²S=5.4); 3.06(3H,s); 3.70(4H,m); 7.11 and 7.30(4H,AB,J=7.2)δ ppm.

Morpholine was used instead of 2,6-dimethyl-morpholine.

N-{3-[4-(1-methoxy-1-methylethyl)-1-phenyl]-2-methylpropyl}-piperidine:
B.p. 104°/0.1 mbar.
IR: 3100–2700, 1900–1550 cm⁻¹;
MS: M+=289(1); m/z: 98(100), 99(5), 96(4), 55(3), 70(2), 41(2), 91(1);
¹HNMR(360 MHz): 0.83(3H,d,J=7); 1.42(2H,m); 1.52(6H,s); 1.57(4H,m); 1.97(1H,m); 2.13(2H,m); 2.23–2.38(5H,m); 2.81(1H,dd,¹J=12.6,²J=4.5); 3.06(3H,s); 7.12 and 7.29(4H,AB,J=7.2)δ ppm.

Piperidine was used instead of 2,6-dimethyl-morpholine.

EXAMPLE 5

N-[3-(4-isopropenyl-1-phenyl)-2-methylpropyl]-piperidine 0.5M of piperidine were added to a cooled solution (10°) of 87 g of 98% formic acid placed in a three-necked flask of 0.5l equipped with a distillation head and kept under nitrogen.

The rate of addition was such that the temperature did not increase beyond 15°. The reaction mixture was then heated to 70° and 0.45M of 3-[4-(1-methoxy-1-methylethyl)-1-phenyl]-2-methylpropanal were added thereto under stirring. CO₂ slowly evolved during addition.

The mixture was then heated to 100° for 2 h while methanol partially distilled. Excess formic acid was distilled off at 100° under reduced pressure, whereupon 76 g of 40% NAOH were added. After cooling, 50 ml of toluene were added to the mixture and the organic phase was separated. After washing with water, the toluene was stripped off and the residue distilled. The desired product was obtained with a yield of about 80%.

B.p. 93°/0.1 mbar.
IR: 3040, 3000–2600, 1900–1600, 1610 cm⁻¹;
MS: M+=257(1); m/z: 98(100), 96(6), 55(4), 91(3), 70(3), 41(3), 131(2);
¹HNMR(360 MHz): 0.84(3H,d,J=7); 1.43(2H,m); 1.58(4H,m); 1.97(1H,m); 2.05–2.21(2H,m); 2.15(3H,s); 2.25–2.41(5H,m); 2.81(1H,dd,¹J=12.5, ²J=5.2); 5.04(1H,s); 5.36(1H,s); 7.12(2H,d,J=7.9) and 7.38(2H,d,J=7.9)δ ppm.

By following the same procedure, but by using morpholine instead of piperdine, N-[3-(4-isopropenyl-1-phenyl)-2-methylpropyl]-morpholine was obtained.

B.p. 103°/0.1 mbar.

IR: 3040, 3000-2600, 1900-1600, 1620 cm$^{-1}$;

MS: M$^+$=259(1); m/z: 100(100), 56(6), 101(5), 91(4), 115(3), 131(2), 70(2); $^1$H NMR(360)MHz): 0.85(3H,d,J"7); 1.96(1H,m); 2.15(3H,s); 208-2.23(2H,m); 2.28-2.46(5H,m); 2.80(1H,dd,$^1$J=12.5, $^2$J=5.8); 3.71(4H,m); 5.04(1H,s); 5.35(1H,s); 7.11(2H,d,J=7.6); 7.38(2H,d,J=7.6)δ ppm.

EXAMPLES OF UTILIZATION

EXAMPLE 6

A perfume composition of cyclamen floral type was prepared by mixing the following ingredients (parts by weight):

| Ingredient | |
|---|---|
| Cinnamic alcohol | 800 |
| Phenylethyl alcohol | 900 |
| α-Ionone | 800 |
| Benzyl acetate | 500 |
| Rose absolute | 200 |
| Amylcinnamic aldehyde | 200 |
| Jasmin absolute | 100 |
| Citral | 100 |
| l-Citronellol | 1900 |
| Heliotropin | 700 |
| Musk ketone | 300 |
| Linalol | 500 |
| Total | 7000 |

The above base composition was used to prepare the following mixtures:

| Ingredient | A | B | C |
|---|---|---|---|
| Base | 700 | 700 | 700 |
| Synth. hydroxycitronellal | 250 | — | 250 |
| Cyclamen aldehyde | 50 | — | — |
| (a) | — | 250 | — |
| (b) | — | 50 | 50 |
| Total | 1000 | 1000 | 1000 |

(a) 3-[4-(1-methoxy-1-methylethyl)-1-phenyl]-2-methylpropanal
(b) 3-(4-isopropenyl-1-phenyl)-2-methylpropanal The mixtures thus obtained were subjected to a comparative evaluation by a panel of perfumery experts who had to assess their respective odor values. Unanimously composition B was found to be the one which possessed the more pronounced flowery note with the more marked fragrance volume. The evaluation of composition B also showed that compound (a) could validly replace hydroxycitronellal while however composition B was rounder and showed more volume and richness when compared to C and did not possess the harshness of A.

EXAMPLE 7

A base composition of lilac floral type was prepared by mixing the following ingredients (parts by weight):

| | |
|---|---|
| Terpineol | 4000 |
| Phenylethyl alcohol | 1200 |
| Linalol | 2000 |
| Anisic aldehyde | 400 |
| Phenylacetaldehyde dimethylacetal | 400 |
| Cinnamic alcohol | 800 |
| Indol 10%* | 200 |
| Total | 9000 |

*diethylphthalate

The above base composition was used to prepare the following compositions by making use of the concentrations indicated in the following table:

| Ingredient | A | B | C | D |
|---|---|---|---|---|
| Base | 900 | 900 | 900 | 900 |
| Lilial (registered trademark)[1] | 100 | — | — | — |
| Cyclamen aldehyde | — | 50 | — | — |
| Dipropylene glycol | — | 50 | — | — |
| (a) | — | — | 100 | — |
| (b) | — | — | — | 100 |
| Total | 1000 | 1000 | 1000 | 1000 |

(a) 3-[4-(1-methoxy-1-methylethyl)-1-phenyl]-2-methylpropanal
(b) 3-(4-isopropenyl-1-phenyl)-2-methylpropanal
[1] p-tert-butyl-α-methyl-hydrocinnamic aldehyde; registered trademark of L. Givaudan As in the previous example, the mixtures obtained were subjected to a comparative evaluation of their odor properties by a panel of perfumery experts which had to assess their respective fragrance character. It appeared that composition C possessed more volume and an enhanced sweetness while being more velvety than the other compositions. Due to the presence of compound (a), composition C possessed a white lilac note while composition D developed a fresh slightly green lilac note.

EXAMPLES 8-20

3-[4-(1-methoxy-1-methylethyl)-1-phenyl]-2-methylpropanal was used in the concentration indicated to perfume a variety of consumer articles as summarized in the following table:

| | Concent. | Odor/Aspect [25° C.] | Odor/Aspect [40° C.]* |
|---|---|---|---|
| 8. Cologne (95° alcohol) | 5.0% | S/N | S/N |
| 9. O/W cream | 0.4% | S/N | S/N |
| 10. W/O cream | 0.4% | S/N | S/N |
| 11. Shampoo | 0.5% | S/N | S/N |
| 12. Deo-spray | 0.8% | S/N | S/N |
| 13. Hair-spray | 0.3% | S/N | S/N |
| 14. Soap | 0.5% | S/N | S/C |
| 15. Talc | 0.5% | S/N | S/C |
| 16. Powdered detergent | 0.2% | S/N | S/N |
| 17. Dish-washing powder | 0.2% | S/N | S/N |
| 18. Roll-on deodorizers | 0.5% | S/N | S/N |
| 19. Hydrogen peroxide | 0.2% | S/N | A/N |
| 20. Permanent wave | 0.5% | S/T | S/T |

Abbreviations:
S = stable
N = normal
A = acceptable
T = turbid
C = coloration
*one month at the indicated temperature The table above summarizes the results of the different perfumery and stability trials carried out by using the mentioned methylpropanal of the invention. The results obtained indicate that the compound is perfectly adapted to act as an effective fragrance ingredient in the manufacture of consumer goods of various nature. Analogous results, albeit in a weaker form, were achieved by the use of the corresponding acetals.

What we claim is:

1. A method for preparing perfume compositions and perfumed articles which comprises adding thereto an odor-effective concentration of an aromatic aldehyde or derivative thereof having the general formula

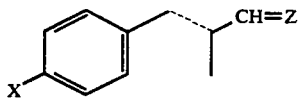

possessing a single or a double bond in the position indicated by the dotted line, wherein X represents a monovalent radical of formula

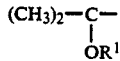 (a.)

or, when the dotted line represents a single bond, of formula

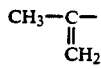 (b.)

and wherein Z stands for an oxygen atom or for two $R^2O$ radicals, $R^1$ and $R^2$ representing an alkyl radical having from 1 to 3 carbon atoms.

2. A perfume composition containing as an odor effective ingredient an aromatic aldehyde or derivative thereof having the general formula

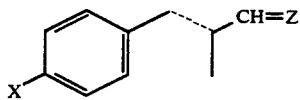

possessing a single or a double bond in the position indicated by the dotted line, wherein X represents a monovalent radical of formula

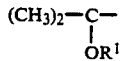 (a.)

or, when the dotted line represents a single bond, for formula

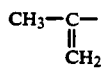 (b.)

and wherein Z stands for an oxygen atom or from two $R^2O$ radicals, $R^1$ and $R^2$ representing an alkyl radical having from 1 to 3 carbon atoms.

3. A perfumed article containing as an odor effective ingredient an aromatic aldehyde or derivative thereof having the general formula

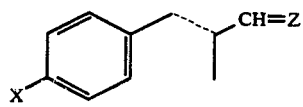

possessing a single or double bond in the position indicated by the dotted line, wherein X represents a monovalent radical of formula

 (a.)

or, when the dotted line represents a single bond, of formula

 (b.)

and wherein Z stands for an oxygen atom or for two $R^2O$ radicals, $R^1$ and $R^2$ representing an alkyl radical having from 1 to 3 carbon atoms.

4. As a perfumed article according to claim 3, a soap, a cosmetic, a body deodorizer, an air-freshener, a detergent, a fabric softener or an household material.

5. The method of claim 1 wherein said aromatic aldehyde or derivative thereof is added in an amount of between about 0.2 and 25 percent by weight.

6. The method of claim 1 wherein said aldehyde is 3-[4-(1-methoxy-1-methylethyl)-1-phenyl]-2-methylpropanal; 3-[4-(1-methoxy-1-methylethyl)-1-phenyl]-2-methylpropionaldehyde dimethylacetal, 3-[4-(1-methoxy-1-methylethyl)-1-phenyl]-2-methylpropionaldehyde diethylacetal, 3-[4-(1-methoxy-1-methyl-2-propenal, 3-(4-isopropenyl-1-phenyl)-2-methylpropanal, 3-(4-isopropenyl-1-phenyl)-2-methylpropionaldehyde dimethylacetal, or 3-(4-isopropenyl-1-phenyl)-2-methylpropionaldehyde diethylacetal.

7. The method of claim 6 wherein the aldehyde is added in an amount of between 0.2 and 5 percent by weight.

8. The composition of claim 2 wherein said aromatic aldehyde or derivative thereof is present in an amount of between about 0.2 and 25 percent by weight.

9. The composition of claim 2 wherein said aldehyde is 3-[4-(1-methoxy-1-methylethyl)-1-phenyl]-2-methylpropanal; 3-[4-(1-methoxy-1-methylethyl)-1-phenyl]-2-methylpropionaldehyde dimethylacetal, 3-[4-(1-methoxy-1-methylethyl)-1-phenyl]-2-methylpropionaldehyde diethylacetal, 3-[4-(1-methoxy-1-methyl-2-propenal, 3-(4-isopropenyl-1-phenyl)-2-methylpropanal, 3-(4-isopropenyl-1-phenyl)-2-methylpropionaldehyde dimethylacetal, or 3-(4-isopropenyl-1-phenyl)-2-methylpropionaldehyde diethylacetal.

10. The composition of claim 9 wherein the aldehyde is present in an amount between 0.2 and 5 percent by weight.

11. The article of claim 3 wherein said aromatic aldehyde or derivative thereof is present in an amount of between about 0.2 and 25 percent by weight.

12. The article of claim 3 wherein said aldehyde is 3-[4-(1-methoxy-1-methylethyl)-1-phenyl]-2-methylpropanal; 3-[4-(1-methoxy-1-methylethyl)-1-phenyl]-2-methylpropionaldehyde dimethylacetal, 3-[4-(1-methoxy-1-methylethyl)-1-phenyl]-2-methylpropionaldehyde diethylacetal, 3-[4-(1-methoxy-1-methyl-2-propenal, 3-(4-isopropenyl-1-phenyl)-2-methylpropanal, 3-(4-isopropenyl-1-phenyl)-2-methylpropionaldehyde dimethylacetal, or 3-(4-isopropenyl-1-phenyl)-2-methylpropionaldehyde diethylacetal.

13. The article of claim 9 wherein the aldehyde is present in an amount of between 0.2 and 5 percent by weight.

* * * * *

UNITED STATES PATENT AND TRADEMARK OFFICE
CERTIFICATE OF CORRECTION

PATENT NO. : 5,086,038

DATED : February 4, 1992

INVENTOR(S) : Ferdinand Naef; Francois Delay; Arnoldus Uijttewaal

It is certified that error appears in the above-identified patent and that said Letters Patent is hereby corrected as shown below:

At col. 3, lines 57-58, change "3-[4-1-methoxy-1-methylethyl)-1-phenyl]-2-methyl-2-propenal" to -- 3-[4-(1-methoxy-1-methylethyl)-1-phenyl]-2-methyl-2-propenal --.

At col. 4, lines 18-19, change "3-[4-(1-methoxy-1-methylethyl)-1-phenyl]-1-phenyl]-2-methylpropanel" to -- 3-[4-(1-methoxy-1-methylethyl)-1-phenyl]-2-methylpropanal --.

At col. 5, line 38, change "than" to -- then --.

In col. 7, delete lines 21-46 since they duplicate the text at from col. 6, line 65 to col. 7, line 19.

At col. 7, lines 49-50, change "N-{3-[4-(1-Methoxy-1-methylethyl)-1)]-2-methyl-propyl}-2,6-dimethylmorpholine" to --N-{3-[4-(1-Methoxy-1-methylethyl)-1-phenyl)]-2-methyl-propyl}-2,6-dimethylmorpholine--.

In claim 6, lines 6-7, claim 9, lines 6-7 and claim 12, lines 6-7, change: "3-[4-(1-methoxy-1-methyl-2-propenal" to -- 3-[4-(1-methoxy-1-methylethyl)-1-phenyl]-2-propenal --.

Signed and Sealed this

Twenty-second Day of June, 1993

Attest:

MICHAEL K. KIRK

Attesting Officer  Acting Commissioner of Patents and Trademarks